United States Patent [19]

Jasserand et al.

[11] Patent Number: 4,672,063

[45] Date of Patent: Jun. 9, 1987

[54] ANTIALLERGIC 5-ALKYL-1-PHENYL-2-PIPERAZINOALK-YLPYRAZOLIN-3-ONE COMPOUNDS

[75] Inventors: Daniel Jasserand; Marie-Odile Christen, both of Paris; Dominique Biard, St. Trivier sur Moignans; Dimitri Yavordios, Chatillon sur Chalaronne, all of France

[73] Assignee: Kali-Chemie Pharma GmbH, Hanover, Fed. Rep. of Germany

[21] Appl. No.: 800,327

[22] Filed: Nov. 21, 1985

[30] Foreign Application Priority Data

Nov. 24, 1984 [DE] Fed. Rep. of Germany ....... 3442860

[51] Int. Cl.$^4$ .................. A61K 31/495; C07D 401/14; C07D 403/06
[52] U.S. Cl. ...................................... 514/252; 540/552; 544/91; 544/364; 544/371; 546/269; 546/277; 548/363; 548/364; 548/367; 548/369; 548/218
[58] Field of Search ................ 544/364, 371; 514/252; 548/363

[56] References Cited

U.S. PATENT DOCUMENTS

| | | | |
|---|---|---|---|
| 3,169,966 | 2/1965 | Schmidt | 544/364 |
| 3,362,956 | 1/1968 | Archer | 544/396 |
| 4,442,102 | 4/1984 | Heinemann et al. | 514/252 |
| 4,515,944 | 5/1985 | Heinemann et al. | 548/363 |
| 4,537,975 | 8/1985 | Heinemann et al. | 544/371 |

FOREIGN PATENT DOCUMENTS

| | | | |
|---|---|---|---|
| 72961 | 3/1983 | European Pat. Off. | 544/371 |
| 72960 | 3/1983 | European Pat. Off. | 544/371 |
| 1473000 | 5/1977 | United Kingdom . | |

OTHER PUBLICATIONS

Jasserand et al., CA 105-153058m.
*Chemical Abstracts Substance Index,* vol. 98, p. 6053CS.
Chemical Abstracts, vol. 98, entry 72018h.
Houden–Weyl, "Methoden der Organischen Chemie", vol. XI/1, fourth edition, pp. 108–111.

*Primary Examiner*—Donald G. Daus
*Assistant Examiner*—Cecilia Shen
*Attorney, Agent, or Firm*—Schwartz, Jeffery, Schwaab, Mack, Blumenthal & Evans

[57] ABSTRACT

5-alkyl-1-phenyl-2-piperazinoalkylpyrazolin-3-one compounds of the Formula

I in which $R_1$ is a straight-chain, branched or cyclic alkyl group with up to 6 carbon atoms, Z is an alkylene chain with 2 to 4 carbon atoms, and 1-phenyl substituent is an optionally substituted phenyl ring, and $R_4$ is a phenyl or pyridyl group which is optionally substituted and their preparation are described. The compounds have pharmacological, particularly antiallergic, properties.

19 Claims, No Drawings

ANTIALLERGIC 5-ALKYL-1-PHENYL-2-PIPERAZINOALKYL-PYRAZOLIN-3-ONE COMPOUNDS

BACKGROUND OF THE INVENTION

This invention relates to new 5-alkyl-1-phenyl-2-piperazinoalkylpyrazolin-3-one compounds and their salts and to pharmaceutical preparations containing these compounds. The invention also relates to methods for preparing these compounds and to intermediates for use in the preparation of these compounds.

U.S. Pat. Nos. 4,442,102 and 4,515,944 disclose 2-piperazinoalkyl-1,5-diphenylpyrazolin-3-one compounds with antiallergic properties.

SUMMARY OF THE INVENTION

It is an object of the present invention to provide new 2-piperazinoalkyl-1-phenylpyrazolin-3-one compounds with valuable pharmacological properties.

These and other objects of the invention are achieved by providing a 5-alkyl-1-phenyl-1-piperazinoalkyl-pyrazolin-3-one compound of the Formula I

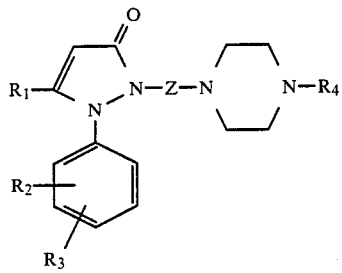

in which
$R_1$ is a straight-chain, branched or cyclic alkyl group with up to 6 carbon atoms,
$R_2$ is hydrogen, halogen, trifluoromethyl, nitro, cyano, hydroxy, lower alkyl, lower alkoxy, or an $R_5$—CO— group, in which $R_5$ is lower alkoxy, lower alkyl or hydroxy, and
$R_3$ is hydrogen, halogen, lower alkyl or lower alkoxy, or
$R_2$ and $R_3$ are linked to adjacent carbon atoms and together form an alkylene-dioxy group with 1 or 2 carbon atoms,
Z is an alkylene chain with 2 to 4 carbon atoms,
$R_4$ is a phenyl group of Formula a or a pyridyl group of Formula b,

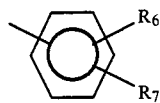 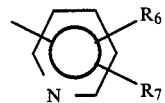

(a)      (b)

in which
$R_6$ is hydrogen, halogen, trifluoromethyl, nitro, cyano, hydroxy, lower alkyl, lower alkoxy or an $R_5$—CO— group in which $R_5$ has the above meaning, and
$R_7$ is hydrogen, halogen, lower alkyl or lower alkoxy, or $R_6$ and $R_7$ are linked to adjacent carbon atoms and together form an alkylene chain with 1 or 2 carbon atoms;
and its acid addition salts.

It has been found that the present 5-alkyl-1-phenyl-2-piperazinoalkylpyrazolin-3-one compounds possess valuable pharmacological properties, in particular marked antiallergic properties with a good therapeutic range and low toxicity, and are distinguished by an improved action profile. Thus, in addition to marked antiallergic properties, the present compounds display peripheral antihistamine and antiserotonin effects and also edema-inhibiting properties.

On the basis of these properties, the new compounds are useful as medicaments in the treatment of allergic disorders, such as for example asthma caused by allergy, hayfever, or inflammations caused by allergy.

DETAILED DESCRIPTION OF PREFERRED EMBODIMENTS

According to one aspect of the present invention there is provided a 5-alkyl-1-phenyl-2-piperazinoalkyl-pyrazolin-3-one compound of the general Formula I

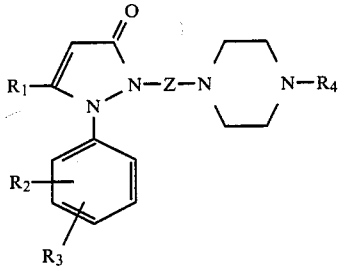

in which
$R_1$ is a straight-chain branched or cyclic alkyl group with up to 6 carbon atoms,
$R_2$ is hydrogen, halogen, trifluoromethyl, nitro, cyano, hydroxy, lower alkyl, lower alkoxy, or an $R_5$—CO— group, in which $R_5$ is lower alkoxy, lower alkyl or hydroxy, and
$R_3$ is hydrogen, halogen, lower alkyl or lower alkoxy, or
$R_2$ and $R_3$ are linked to adjacent carbon atoms and together form an alkylene-dioxy group with 1 or 2 carbon atoms,
Z is an alkylene chain with 2 to 4 carbon atoms,
$R_4$ is a phenyl group of Formula a or a pyridyl group of Formula b,

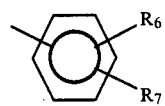 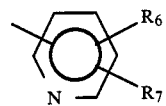

(a)      (b)

in which
$R_6$ is hydrogen, halogen, trifluoromethyl, nitro, cyano, hydroxy, lower alkyl, lower alkoxy or an $R_5$—CO— group in which $R_5$ has the above meaning, and
$R_7$ is hydrogen, halogen, lower alkyl or lower alkoxy, or $R_6$ and $R_7$ are linked to adjacent carbon atoms and together form an alkylene chain with 1 or 2 carbon atoms;

and its acid addition salts.

In the compounds of Formula I, where the substituents $R_2$, $R_3$ and $R_4$ represent substituents containing lower alkyl groups, these may be straight or branched and contain 1 to 4, preferably 1 or 2 carbon atoms.

Where the substituents $R_2$, $R_3$ and $R_4$ represent or contain halogen, the following halogens are prepared, namely fluorine, chlorine and bromine.

The substituents $R_2$ and/or $R_3$ of the phenyl ring are preferably hydrogen, halogen, in particular chlorine, nitro, cyano, hydroxy, lowr alkyl, in particular methyl, lower alkoxy, in particular methoxy or ethoxy, or lower alkyl- or alkoxycarbonyl, in particular acetyl, methoxycarbonyl or ethoxycarbonyl. Thus, for example, preferred compounds are those in which $R_3$ is hydrogen and $R_2$ is hydrogen, halogen, in particular chlorine, nitro, lower alkoxy, in particular methoxy, or lower alkylcarbonyl, in particular acetyl, and is preferably arranged in position 4 or in position 2.

If $R_4$ is a phenyl of Formula a

(a)

$R_6$ and/or $R_7$ preferably represent hydrogen, halogen, in particular fluorine or chlorine, trifluoromethyl, lower alkyl, in particular methyl, or lower alkoxy, in particular methoxy. Particularly suitable compounds are those in which $R_7$ is hydrogen and $R_6$ is hydrogen or halogen, in particular fluorine, and is preferably arranged in position 4 or in position 2. The 4-fluorophenyl radical is particularly favorable.

If $R_4$ is a pyridyl group of Formula b

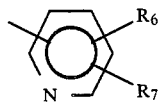

(b)

the 2-pyridyl group is preferred. In the pyridyl group, $R_7$ is preferably hydrogen and $R_6$ is hydrogen, lower alkyl, in particular methyl, or halogen, in particular chlorine. The 4-methyl-2-pyridyl group is particularly advantageous.

$R_1$ is a straight-chain, branched or cyclic alkyl group with up to 6 carbon atoms. Suitable cyclic alkyl groups may contain 3 to 6, preferably 5 or 6 carbon atoms and include e.g. cycloalkyl groups such as cyclopropyl, cyclopentyl or preferably cyclohexyl. Non-cyclic alkyl groups may be straight-chain or branched and contain 1 to 6 carbon atoms, preferably 1 to 4 carbon atoms and more preferably 1 to 3 carbon atoms. Examples of suitable non-cyclic alkyl groups are methyl, ethyl, straight-chain or branched propyl or butyl groups and butyl substituted by methyl or ethyl. Of these, straight-chain alkyl radicals with 1 to 3 carbon atoms, in particular methyl or ethyl, are preferred.

Z is an alkylene chain with 2 to 4 carbon atoms, which may be straight-chained or may represent a chain substituted by methyl, and contains in particular 3 or 5 carbon atoms. Preferably Z is a propylene chain.

According to another aspect of the present invention there is provided a method for the preparation of 5-alkyl-1-phenyl-1-piperazinoalkylpyrazolin-3-one compound of the general Formula I

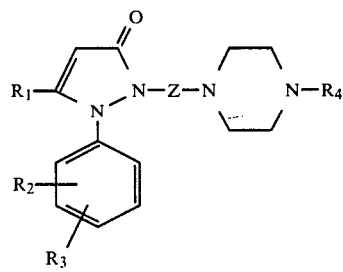

I in which $R_1$ is a straight-chain, branched or cyclic alkyl group with up to 6 carbon atoms, $R_2$ is hydrogen, halogen, trifluoromethyl, nitro, cyano, hydroxy, lower alkyl, lower alkoxy, or an $R_5$—CO— group, in which $R_5$ is lower alkoxy, lower alkyl or hydroxy, and $R_3$ is hydrogen, halogen, lower alkyl or lower alkoxy, or $R_2$ and $R_3$ are linked to adjacent carbon atoms and together form an alkylene-dioxy group with 1 or 2 carbon atoms, Z is an alkylene chain with 2 to 4 carbon atoms, $R_4$ is a phenyl group of Formula a or a pyridyl group of Formula b,

 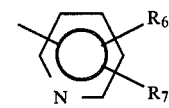

(a) (b)

in which $R_6$ is hydrogen, halogen, trifluoromethyl, nitro, cyano, hydroxy, lower alkyl, lower alkoxy or an $R_5$—CO— group in which $R_5$ has the above meaning, and $R_7$ is hydrogen, halogen, lower alkyl or lower alkoxy, or $R_6$ and $R_7$ are linked to adjacent carbon atoms and together form an alkylene chain with 1 or 2 carbon atoms;

and it acid addition salts, comprising the step of (a) reacting a compound of Formula II or III

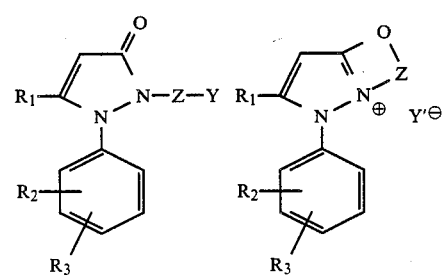

II III in which $R_1$, $R_2$, $R_3$ and Z have the above meanings, Y is a group that can be split off by aminolysis and Y' is halogen or a mixture of the compounds of Formula II or III with a compound of Formula IV

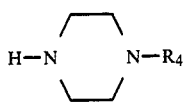   IV in which $R_4$ hs the above meaning, or (b) in order to prepare a compound of the general Formula Ia

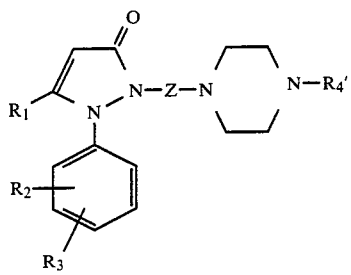   Ia in which $R_1$, $R_2$, $R_3$ and Z have the above meanings and $R_4'$ is a substituted phenyl group a'

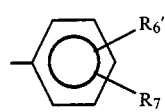   a' in which $R_7$ has the above meaning and $R_6'$ is in ortho- or para- position and is trifluoromethyl or nitro, or $R_4'$ is a 2-pyridyl group of Formula b'

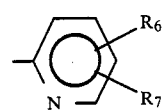   b' in which $R_6$ and $R_7$ have the above meanings, reacting a compound of Formula V

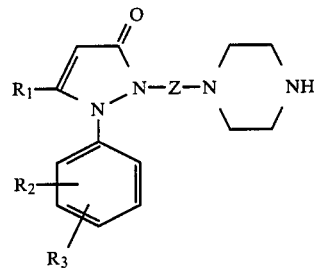   V in which $R_1$, $R_2$, $R_3$ and Z have the above meanings, with a compound of Formula VI Hal—$R_4'$   VI in which $R_4'$ has the above meaning and Hal is halogen, or (c) in order to prepare a compound of the general Formula Ib

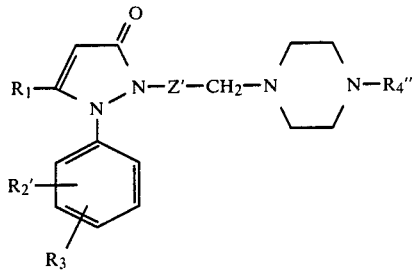   Ib in which $R_1$ and $R_3$ have the above meanings, $R_2'$ and $R_4''$ have the meanings given for $R_2$ and $R_4$ with the exception of cyano and of radicals containing a cyano or carbonyl group, and Z' is an alkylene chain with 2 or 3 carbon atoms, reducing a compound of Formula VII

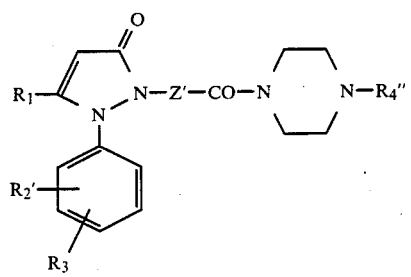   VII in which $R_1$, $R_2$, $R_3$, $R_4''$ and Z' have the above meanings, and thereafter comprising one or more of the following optional steps (i) converting a methoxy group in the compound of Formula I into hydroxy, (ii) converting an alkoxy carbonyl group in the compound of Formula I into carboxy, (iii) converting a free compound of Formula I into its acid addition salt, or (iv) converting an acid addition salt of the compound of Formula I into the free compound of Formula I.

The reaction of the compound of Formula II or III or a mixture thereof with the compound of Formula IV according to method variant (a) may be carried out by methods conventional per se for the alkylation of amines.

The reaction is expediently carried out under basic conditions in an organic solvent which is inert under the reaction conditions. Halogens such as chlorine, bromine or iodine, preferably chlorine or bromine, are suitable as radicals that can be split off by aminolysis from the compounds of Formula II. Examples of suitable solvents include aromatic hydrocarbons such as toluene, xylene or benzene, cyclic ethers such as dioxane, dimethylformamide, sulpholane, dimethylsulphoxide, tetramethylurea or lower alkanols such as isopentanol. The reaction may be carried out at a temperature of from ambient temperature to 150° C., preferably at elevated temperature, e.g. at a temperature of from 50° to 150° C., more preferably at the boiling temperature of the solvent.

If desired, the reaction of the compound of Formula II or III with the compound of Formula IV may also take place in a solvent-free melt. Advantageously, the reaction may be carried out with the addition of an organic or inorganic base. However, an excess of the compound of Formula IV may be used and this may be utilized as an internal base. Alkali metal carbonates and bicarbonates are examples of particularly suitable inorganic bases. Tertiary organic amines, in particular tertiary lower alkylamines such as triethylamine, 1,4-dimethylpiperazine or pyridine are examples of suitable organic bases.

If the compounds of Formulae II, III or IV contain free hydroxy or carboxyl group substituents, these are advantageously provided, during the reaction, in a manner known per se, with a protective group. Suitable protective groups, which can be easily split off again after the reaction, are known for example from E. McOmie "Protective Groups in Organic Chemistry," Plenum Press 1971. Ethers, in particular tetrahydropyran, are suitable for example for the protection of a hydroxyl function. Lower alkyl esters are suitable for the protection of the carboxyl function. These protective groups may be easily removed again in a manner known per se after the reaction.

The reaction of the compound of Formula V with the compound of Formula VI according to method variant (b) may likewise take place in a manner known per se under conventional conditions for the alkylation of amines, for example under the conditions named above for the reaction of the compound of Formula II with the compound of Formula IV. The substituted halogenated phenyl groups of Formula VI are sufficiently activated by the presence of a second order substituent, to be capable of the reaction with the piperazine derivative of Formula V. Likewise, the 2-halopyridine compounds of Formula VI are capable of reacting with the piperazine derivative of Formula V.

The reaction of the compound of Formula VII according to method variant (c) may be carried out in a manner known per se according to methods conventional for the reduction of amide groups. Suitable reducing agents for use in such methods include hydride reducing agents such as diborane or sodium borohydride in a weakly acid medium, lithium borohydride or lithium aluminum hydride. The reduction with sodium borohydride may be carried out for example in a solvent which is inert under the reaction conditions, in a weakly acid pH range. Suitable solvents include, for example, cyclic or open ethers such as dioxane, tetrahydrofuran, ethylene glycol dimethylether or diethylene glycol dimethylether as well as dimethylformamide or low molecular weight alcohols. Organic or inorganic acids such as e.g. acetic acid, aromatic sulphonic acids or hydrochloric acid may be used for adjusting the pH into a favorable range in each case. The method variant (c) is suitable in particular for the preparation of these compounds of Formula I, in which Z is the butylene chain.

If it is desired to convert a methoxy substituent into a hydroxy group this can be effected by methods conventional per se for splitting ethers. Likewise conversion of an alkoxycarbonyl substituent into a carboxyl group may take place in a manner known per se according to conventional methods for ester hydrolysis.

The compounds of Formula I may be isolated from the reaction mixture and purified in a manner known per se. Acid addition salts may be converted in a conventional manner into the free bases and these, if desired, may be converted in a known manner into pharmacologically compatible acid addition salts.

Suitable pharmacologically acceptable acid addition salts of compounds of Formula I include, for example, the salts with inorganic acids such as hydrochloric acid, hydrobromic acid, sulphuric acid and phosphoric acid or with organic acids such as methane sulphonic acid, ethane sulphonic acid, benzene sulphonic acid, p-toluene sulphonic acid, acetic acid, lactic acid, citric acid, succinic acid, maleic acid, fumaric acid, malic acid, tartaric acid, benzoic acid, phenlyacetic acid and mandelic acid.

The compounds of Formula I contain several basic centers and may therefore form acid addition salts with several equivalents of acid. For the production of pharmaceutical preparations, mono-acid salts are particularly suitable. Salts which contain several equivalents of acid may, if desired, be converted in a manner known per se, into mono-acid salts, e.g. by conversion into the free base and subsequent reaction of the base with an equivalent quantity of acid. Insofar as the mono-acid salt is minimally water-soluble, it may also be precipitated out through slow and careful alkalinization of an acidified (preferably pH 4) aqueous solution of the base or salts thereof containing several equivalents of acid.

Compounds of Formula I, in which Z represents a branched alkylene chain, are obtained in the form of their racemates. The present invention includes the racemic mixtures as well as optically active forms of these compounds. The optically active compounds may be separated from the racemic mixtures in a manner known per se through reaction with suitable optically active acids, such as for example tartaric acid, and subsequent fractional crystallization of the recovered salts into their optically active antipodes.

Compounds of Formulae II and III have not been described to date in the literature and therefore represent new valuable intermediate products for the preparation of pharmacologically active compounds, for example the compounds of Formula I.

Compounds of Formulae II and III may be obtained according to methods known per se. Thus, for example, a compound of Formula II, in which Y is halogen, or a compound of Formula III may be obtained by reacting an alkali metal salts, produced in situ, of a 5-alkyl-1-phenylpyrazoline-3-one compound of Formula VIII

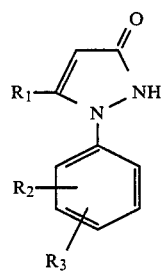

VIII in which $R_1$, $R_2$ and $R_3$ have the above meanings, with a compound of Formula IX

IX in which Z, Y and Y' have the above meanings. Y' and Y are preferably each chlorine or bromine.

The reaction expediently takes place in a solvent which is inert under the reaction conditions, at a temperature of from 0° C. up to the boiling temperature of the solvent. In general, a temperature of from 0° to 120° C. is advantageous. Suitable solvents include, for example, lower alcohols such as methanol, ethanol, isopropanol and butanols, aromatic hydrocarbons such as benzene and toluene, dimethylformamide, sulpholane, hexamethyl phosphorus triamide, tetramethylurea and cyclic ethers such as dioxane or tetrahydrofuran.

Suitable alkali metal salts of the compounds of Formula VIII include the lithium, sodium and potassium salts, preferably the sodium salt, which may be obtained in situ by reacting the compound of Formula VIII with an alkali metal alcoholate or alkali metal hydride.

In addition to the open alkylation products of Formula II, cyclic alkylation products of Formula III are obtained as a result of the reaction. The compounds II and III are present in the reaction mixture in variable quantitative proportions, depending upon the solvents and alkali metal compounds used, the reaction time, the identities of the individual substituents and the chain length of the substituent Z. Thus, for example, when using a lower alcohol and the corresponding alkali metal alcoholate and lengthy reaction times, for example 15 to 35 hours, the cyclic compounds of Formula III are preferentially formed, particularly if Z represents a propylene chain. When using dimethylformamide and alkali metal hydrides and shorter reaction times, for example 1 to 15 hours, on the contrary the compounds of Formula II are predominantly produced. Since both compounds II and III or mixtures thereof may be used in the subsequent reaction, separation of the two compounds before further reaction is not necessary. Of course, however, the cyclic compounds of Formula III may be separated from the open-chain products of Formula II in a manner known per se through crystallization or chromatographic separation methods.

As a result of the alkylation of the 5-alkyl-1-phenyl-pyrazoline-3-one compounds of Formula VIII with the compounds of Formula IX, mixtures of the desired N-alkylated products and the O-alkylated products isomeric therewith are generally obtained. From these mixtures, the N-alkylated product can be separated chromatographically or by crystallization. The O-alkylated by-products may be rearranged by simple heating into the corresponding N-alkylated products of Formula II and/or the cyclic immonium salts of Formula III. The rearrangement temperature is desirably from 60° to 200° C. If desired, the rearrangement may be carried out in the presence of an inert solvent, advantageously at the boiling temperature of the solvent. Suitable solvents include lower alcohols, boiling in the given range, for example methanol, one of the butanols and isopentanol, or aromatic hydrocarbons such as benzene, toluene and xylene. The mixtures of cyclic immonium compounds III, N-alkylated products II and the O-alkylated products which are isomeric therewith, obtained on alkylation, may be subjected directly without prior separation to the thermal rearrangement reaction.

Compounds of Formula V have not been described in the literature to date and are also new valuable intermediates for the preparation of pharmacologically active compounds, for example compounds of Formula I.

Compounds of Formula V may be obtained by methods known per se, for example by reacting a compound of Formulae II or III with an excess of piperazine. The reaction may be carried out according to methods conventional per se for the alkylation of amines, for example under the conditions described above for the reaction of compounds of Formulae II and III with compounds of Formula IV.

Compounds of Formula V may also be obtained from compounds of Formula X

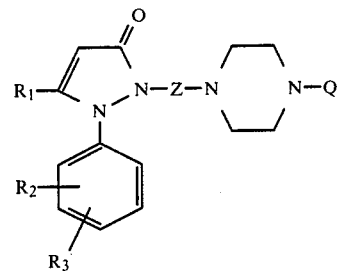

in which $R_1$, $R_2$, $R_3$ and Z have the above meanings and Q is an amine-protecting group, in which the amine-protecting group is split off in a manner known per se. The amine-protecting group may be one of the conventional protective groups, known per se for the protection of an amino function, such as for example removable benzyl groups. Suitable protective groups are known, for example, from E. McOmie "Protective Groups in Organic Chemistry," Plenum Press, London (1971) p. 44 ff. Particularly suitable protective groups are the formyl group and lower carbalkoxy groups. These may be split off in a manner known per se by acid or alkaline hydrolysis.

Compounds of Formula X may be obtained in a manner known per se, for example by reacting a compound of Formula II or III with a compound of Formula XI

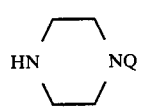

in which Q has the above meaning.

Compounds of Formula VII have not been described in the literature to date and represent new valuable intermediates for the preparation of pharmacologically active compounds, for example the compounds of Formula I. Compounds of Formula VII may be obtained in a manner known per se using as starting materials, the coresponding compounds of Formula II or III or mixtures thereof. Thus, for example, compounds of Formulae II and/or III may be first reacted with an alkali metal cyanide to form a nitrile of Formula XII

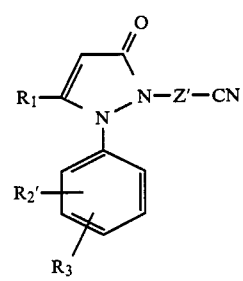

in which $R_1$, $R_2'$, $R_3$ and $Z'$ have the above meanings, and the nitrile is converted by acid hydrolysis into the corresponding carboxylic acid of Formula XIII

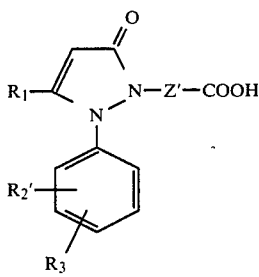

in which $R_1$, $R_2'$, $R_3$ and $Z'$ have the above meanings, and the latter acid is subsequently reacted with a corresponding piperazine compound of Formula IV to form the amide compounds of Formula VII.

The reaction of the compound of Formula II or III with the alkali metal cyanide, preferably sodium cyanide, expediently takes place in a solvent which is inert under the reaction conditions, for example dimethylformamide, at elevated temperature, preferably the boiling temperature of the solvent. The hydrolysis of the nitrile of Formula XIII to the corresponding carboxylic acid may take place under acid conditions by methods conventional per se for nitrile hydrolysis, for example by treatment with an aqueous mineral acid. The reaction of the carboxylic acid of Formula XIII with the piperazine compound of Formula IV takes place according to methods conventional per se for amide formation. Expediently, the carboxylic acid of Formula XIII is first converted in situ into a reactive derivative, for example by reaction with ethyl chloroformate, and the resulting reactive acid derivative is then immediately further reacted with the piperazine of Formula IV. The reaction preferably takes place in a solvent which is inert under the reaction conditions, for example a halogenated hydrocarbon such as chloroform, at a temperature of from $-10°$ C. to ambient temperature. Expediently, the reaction may be carried out with the addition of an organic or inorganic base. However, an excess of the compound of Formula IV may also be used an this may be utilized as an internal base. Suitable organic bases include tertiary organic amines, in particular tertiary lower alkylamines, such as triethylamine.

The 5-alkyl-1-phenyl-pyrazoline-3-ones of Formula VIII are known or may be prepared according to methods known per se. For example, the compounds may be obtained using as starting materials corresponding acylacetic acid esters and correspondingly substituted β-acetyl-phenyl-hydrazines according to the method described by K. Mayer (Ber., 36 (1903), 717). In addition, the compounds of Formula VIII may also be obtained according to the method described by L. Lederer (J. Prakt. Chem., 27 (1892), 83) by the oxidation of corresponding 5-alkyl-1-phenyl-pyrazolin-3-ones, which in turn may be produced by reacting corresponding β-halogen carboxylic acids with correspondingly substituted phenyl hydrazines and subsequent cyclizing, or by reacting correspondingly substituted acrylic acid esters or amides with correspondingly substituted phenylhydrazines (see U.S. Pat. Nos. 2,688,024 and 2,704,762).

Compounds of Formula IV are known or may be prepared according to methods known per se, for example by reacting amines of Formula XIV $$H_2N-R_4 \qquad XIV$$

in which $R_4$ has the above meaning, with di(2-haloethyl)-amines under conventional conditions for the alkylation of amines.

The compounds of Formula I and their pharmacologically acceptable acid addition salts possess interesting pharmacological properties, in particular marked antiallergic properties, and are distinguished by a favorable action profile, good compatibility and low toxicity. Thus, in addition to an inhibiting effect on allergic reactions induced by antigens, the compounds also show a marked effect against allergic reactions of the skin induced by endogenous mediators such as histamine and serotonin, and have an inhibiting effect with respect to the release of endogenous mediators from the mast cells leading to allergic reactions. In addition, the compounds have edema-inhibiting properties.

The antiallergic and antiedematous properties of the compounds of Formula I may be demonstrated in standard pharmacological tests on animals.

For example, the compounds display a specific inhibiting effect in the PCA test (passive cutaneous anaphylaxis), described below, on the rat. The peripheral antihistamine and antiserotonin effects may likewise be demonstrated in the same test arrangement through the inhibiting effect on anaphylactoid reactions of the skin induced by histamine or serotonin. The inhibiting effect on the release of histamine from the mast cells, caused anaphylactically, may be demonstrated for example in vitro on isolated peritonal mast cells.

DESCRIPTION OF THE TEST METHODS

1. Acute Toxicity

The acute 8-day toxicity is determined after a single application i.p. to male mice (body weight 18 to 22 g). The mortality is noted for 8 days. The results are calculated as $LD_{50}$ values, i.e. the dose which kills 50% of the animals.

2. Determining the inhibition of passive cutaneous anaphylaxis (PCA) and the inhibition of anaphylactoid cutaneous reactions induced by histamine and by serotonin.

For the preparation of an antiovalbumin serum, rich in IgE, which is used in the test, according to the method of Lehrer et al (J. Immunol. 116, (1976) 178–182) and Pauwels et al (Ann. Immunol. 230C., (1979), 49–58), Sprague-Dawley rats are sensitized by i.p. injection of 1 mg ovalbumin and 1 ml Bordetella pertussis suspension (vaxicoq, Merieux $3 \times 10^{10}$ organisms/ml). After 20 days the animals are given an injection of 10 mg ovalbumin in the same way, but without any additive. After a further 4 days, blood is removed from the animals and the blood is centrifuged. The antiserum thus obtained is stored at $-20°$ C. and adjusted according to the method of Goose et al (Immunology 16 (1968) 749–760).

The determination of the inhibition of passive cutaneous anaphylaxis and the anaphylactoid cutaneous reactions induced by histamine and by serotonin, are carried out, as set forth below, according to the method of Martin and Baggiolini (Naunyn-Schmeiedeberg's Archives of Pharmacology 316 (1981) 186–189).

For passive sensitizing against ovalbumin, male Sprague-Dawley rates (body weight 150 to 165 g) are injected intradermally on a shaved part of the back with 0.05 ml of a 1:2.5 dilution of antiovalbumin serum, rich in IgE, in physiological sodium chloride solution.

24 hours after the sensitizing, solutions of the test substances are administered orally to the rats. For comparison, a control group receives only the solvent.

To trigger the histamine-induced and serotonin-induced anaphylactoid reactions of the skin, the animals are injected intradermally 30 minutes later on a second shaved part of the back with a solution of 40 μg histamine in 0.05 ml physiological sodium chloride solution and on a third shaved part of the back with a solution of 1 μg serotonin in 0.05 physiological sodium chloride solution.

Immediately thereafter 1.25 mg ($\triangleq$~8 mg/kg) ovalbumin to trigger the anaphylactic reaction, and 4 mg ($\triangleq$~26.4 mg/kg) of a blue dye dissolved in 0.5 ml phosphate-buffered physiological sodium chloride solution are administered i.v. to the animals.

After 30 minutes the animals are killed, the skin is removed and in the individual blue patches the quantity of dye contained therein is determined separately. According to the method of Mordelet-Danbrine et al (Therapie 29 (1974) 851–862) the dye is extracted from the individual patches in each case with 2.5 ml dimethylformamide at a temperature of 37° C. for 4 days and the quantity of dye obtained in each case in the extraction solution is determined by spectrophotometric measurement. The doses of the test substances which cause a 50% reduction in the dye concentration compared with the control group are calculated as $ED_{50}$ values.

3. Determining the inhibiting effect in vitro on the release of histamine, caused anaphylactically, from peritonal mast cells of rats.

In order to obtain the peritonal mast cells, Sprague-Dawley rats are killed by inhalation of ether and immediately after cessation of breathing has occurred, 15 ml of a cold solution of 1 mg/ml human serum albumin in phosphate-buffered sodium chloride solution are injected into the abdominal cavity. The peritonal fluid is then removed and the mast cells are separated therefrom by centrifuging and are suspended in phosphate-buffered sodium chloride solution, whereafter the suspension is adjusted to a mast cell concentration of $5 \times 10^5$ per ml.

The mast cell suspension, divided up into samples each of 100 μl, is introduced into test-tubes and each sample, for passive sensitizing, is mixed with 100 μl of a 1:10 dilution of IgE-rich antiovalbumin serum in physiological sodium chloride solution (prepared according to the method described above) and is incubated for 30 minutes at a temperature of 37° C. (water bath). For the removal of unbonded IgE, the mast cells are then washed with 2 ml phosphate-buffered sodium chloride solution, centrifuged, and the supernatant fluid is discarded. Then the mast cells are incubated for 1 minute at 37° C. with 200 μl of a solution of the test substance in phosphate-buffered sodium chloride solution. A control group is only incubated with the same quantity of phosphate-buffered sodium chloride solution which is free of test substance.

In order to trigger the anaphylactically caused release of histamine, 200 μl of a solution of 100 μg/ml ovalbumin in phosphate-buffered sodium chloride solution are added to the mast cells which have been thus treated. After an incubation period of 3 minutes at 37° C., the reaction is stopped by rapid cooling in an ice bath. Then centrifuging takes place, the supernatant fluid is decanted and the histamine content therein is determined directly, without further extraction, spectrofluorimetrically according to the method of Shore (J. Pharmac. Exp. Ther. 127 (1959) 182–186).

For the extraction of the residual histamine still contained in the mast cells of the undecanted material, the latter is mixed with 2 ml phosphate-buffered sodium chloride solution and the suspension is heated in a boiling water bath. Then centrifuging takes place, the supernatant fluid is decanted and therein the residual histamine extracted from the mast cells is determined spectrofluorimetrically.

For each sample, the quantity of the released histamine is calculated as percentage proportion of the overall quantity of histamine (=total of released histamine and residual histamine retained in the mast cells).

The $EC_{50}$ values are calculated to be those molar concentrations of the test substances in the respective test solutions which produce a 50% inhibition of the histamine release compared to the control group.

The following Tables A and B show results obtained according to the test methods described above. The Example numbers given for the compounds of Formula I refer to the subsequent synthesis Examples.

TABLE A

Inhibiting effect with respect to cutaneous allergic reactions in the rat, $ED_{50}$ mg./kg. p.o.

| Test Subst. Ex. No. | passive cutaneous anaphylaxy | histamine-induced anaphylactoidal reaction | serotonin induced anaphylactoidal reaction | Acute toxicity mg/kg mouse i.p. |
|---|---|---|---|---|
| 1 | 2.5 | 4.7 | 2.6 | 117 |
| 2 | 1.9 | 1.75 | 2.7 | 90 |
| 4 | 3.9 | 7.98 | 5.9 | 130 |
| 7 | 6.6 | 7.9 | 13.0 | 178 |
| 11 | 4.65 | 10.1 | 10.2 | 108 |
| 13 | 2.94 | 5.48 | 1.87 | 96 |
| 15 | 1.9 | 4.4 | 1.7 | 90 |
| 17 | 5.0 | 12.6 | 10.8 | 342 |
| 18 | 4.7 | 6.6 | 6.2 | 205 |
| 21 | 7.1 | 5.1 | 8.3 | 252 |
| 23 | 7.85 | 4.7 | 5.8 | 168 |
| 26 | 6.75 | 6.3 | 7.8 | 72.5 |
| 38 | 3.18 | 3.88 | 5.54 | 93 |
| 39 | 5.7 | 9.7 | 2.5 | 91.5 |
| 43 | 2.45 | 5.79 | 3.25 | |
| 44 | 5.4 | 3.15 | 8.9 | 170 |
| 45 | 6.3 | 11 | 8.0 | 240 |
| 46 | 6.3 | 2.8 | 8.0 | 101 |
| 47 | 5.96 | 6.8 | 6.8 | 190 |
| 49 | 4.9 | 10.6 | 3.59 | 96 |
| 54 | 4.45 | 5.46 | 0.52 | 53.3 |
| 55 | 7.26 | 11.86 | 11.80 | 135 |
| 56 | 5.7 | 3.85 | 6.29 | >350 |
| 58 | 1.17 | 10 | 1.41 | 95 |
| 60 | 1.86 | 3.32 | 2.49 | 91.5 |
| 62 | 5.47 | 7.04 | 3.64 | |

TABLE B

| Test substance Example No. | in vitro inhibiting effect with respect to anaphylactically caused histamine release from mast cells of the rat $EC_{50}$ mol./l. |
|---|---|
| 1 | $5 \times 10^{-5}$ |
| 15 | $1.4 \times 10^{-5}$ |
| 18 | $23 \times 10^{-5}$ |
| 20 | $1.0 \times 10^{-5}$ |
| 22 | $4.3 \times 10^{-5}$ |
| 23 | $14 \times 10^{-5}$ |
| 26 | $3.5 \times 10^{-5}$ |
| 30 | $1.8 \times 10^{-5}$ |
| 49 | $5.7 \times 10^{-5}$ |
| 54 | $12 \times 10^{-5}$ |
| 58 | $12 \times 10^{-5}$ |
| 60 | $20 \times 10^{-5}$ |

TABLE B-continued

| Test substance Example No. | in vitro inhibiting effect with respect to anaphylactically caused histamine release from mast cells of the rat EC$_{50}$ mol./l. |
| --- | --- |
| 62 | 6.2 × 10$^{-5}$ |

The antiedematous properties of the compounds of Formula I can be demonstrated by their inhibiting effects with respect to local formation of edema caused by carrageenin injection in the rat's paw.

Description of the test method to determine the inhibiting effect on the carrageenin edema of the paw in the rats according to the method of Winter et al (Proc. Soc. Exp. Biol. Med. 111 (1962) 544–547).

Male Wistar rates with a body weight of approximately 120 to 140 g are used. A dose of 100 mg/kg of the test substance suspended in a volume of 0.5 ml per 100 g body weight of a 1% methyl cellulose solution Tylose ®, American Hoechst Corp., Somerville, NJ) is administered per os.

Only the Tylose ® solution is administered to a control group. One hour later, to initiate the inflammation, 0.1 ml of a 1% suspension of carageenin (Satiagum ® E) in an isotonic solution of sodium chloride are administered as an irritant by intraplantar injection into the right rear paw. An identical volume of isotonic sodium chloride solution is injected into the left rear paw. Both before and also 3 hours after the administration of the irritant, the volume of the individual rat paws is measured plethysmometrically and the volume of swelling of the paw after administration of carrageenin is determined compared with the paw which was only treated with sodium chloride solution. The inhibition of edema formation brought about by the test substances in the treated animals is indicated in percentage compared with the animals of the untreated control group.

The following Table C shows results obtained according to the method described above, with compounds of Formula I.

TABLE C

| Test Substance Example No. | % Inhibition of carageenin paw edema in the rat at a dose of 100 mg/kg/p.o. |
| --- | --- |
| 1 | 52.8 |
| 8 | 56.4 |
| 12 | 49.5 |
| 39 | 42.6 |
| 54 | 45.6 |
| 59 | 45.7 |
| 60 | 62.4 |
| 62 | 63.9 |
| 63 | 42.2 |

On the basis of their antiallergic effects and their peripheral antihistamine and antiserotonin effects and their edema-inhibiting properties, the compounds of Formula I and their pharmacologically acceptable acid addition salts are useful as antiallergic agents for the treatment of allergic disorders such as, for example, bronchial asthma or allergic rhinitis and also allergically caused inflammations.

As medicines, compounds of Formula I and their pharmacologically compatible salts may be contained, together with conventional pharmaceutical adjuvant substances, in galenical preparations such as, for example, tablets, capsules, suppositories, ointments, solutions or sprays. These galenical preparations may be produced according to methods known per se using conventional solid or liquid carriers or diluents, including solids such as, for example, talcum, lactose and starch, or liquids such as, for example, water, fatty oils and liquid paraffins.

The compounds of Formula I may be put up in pharmaceutical forms for administration which contain 0.5 to 100 mg preferably 0.5 to 25 mg active substance per individual dose. The dosage which is to be used is, of course, adapted to the species which is to be treated and to individual requirements. Parenteral formulations will generally contain less active substance than preparations which are to be administered orally.

The following Examples are intended to explain in further detail the preparation of the new compounds of Formula I and of the new intermediates, but are not to restrict the scope of the invention in any way.

The structures of the new compounds were ascertained by spectroscopic investigations, in particular by an accurate analysis of the IR- and NMR-spectra.

EXAMPLE 1

5-ethyl-1-phenyl-2- {3-[4-(4-fluorophenyl)-piperazin-1-yl]-propyl}-pyrazolin-3-one (A) 21 g 5-ethyl-1-phenylpyrazolin-3-one are suspended in 250 ml methanol. A sodium methylate solution produced from 2.7 g in 50 ml methanol is added to this suspension, with stirring, at ambient temperature. After stirring for 30 minutes, a clear solution is produced. 18.5 g 1-bromo-3-chloropropane are added dropwise to the solution and the mixture is then heated for 24 hours under reflux. Then the solvent is evaporated off, the residue is extracted with 300 ml methylene chloride, the organic phase is washed three times with 30 ml water in each case, and the washing waters are extracted with 20 ml methylene chloride. The methylene chloride phases are combined, dried over sodium sulphate and filtered. The solution is concentrated to dryness by evaporation and the remaining residue is treated with acetone and then with ethyl acetate. 7.5 g 2-ethyl-1-phenyl-6,7-dihydro-1H,-5H-pyrazolo (5,1-b)(1,3)-oxazin-8-ium-chloride are obtained, with a melting point of 203°–204° C. A further 6 g of the same immonium salt are obtained by extraction with methylene chloride of the residue obtained after concentration of the washing water phases by evaporation. Total yield of immonium salt: 13.5 g.

(B) A suspension of 6.61 g of the immonium salt described under A, 4.68 g 1-(4-fluorophenyl)piperazine and 4.35 g sodium carbonate in 188 ml toluene is heated with stirring for 8 hours under reflux. Then the reaction mixture is cooled, washed with 100 ml water, the organic solution separated off and extracted with 100 ml 25% hydrochloric acid solution. The aqueous acid solution is made alkaline by the addition of sodium hydroxide and the resulting base is extracted with methylene chloride. The organic phase is dried over sodium sulphate, filtered and the solvent drawn off under reduced pressure. The remaining oil is crystallized from isopropyl ethyl/cyclohexane. 6 g 5-ethyl-1-phenyl-2-{3-[4-(4-fluorophenyl)-piperazin-1-yl]-propyl}-pyrazolin-3-one are obtained. Melting point 70°–71° C.

EXAMPLE 2

5-methyl-1-(4-nitrophenyl)-2-{3-[4-(4-methyl-pyrid-2-yl)-piperazin-1-yl]-propyl}-pyrazolin-3-one (A) 26.5 g 5-methyl-1-(4-nitrophenyl)-pyrazolin-3-one are suspended in 200 ml methanol. A sodium methylate solution obtained from 3 g sodium and 100 ml methanol is added dropwise. 20.5 g 1-bromo-3chloropropane are added to the resulting clear solution at ambient temperature. The solution is heated for 72 hours with stirring under reflux. After cooling, the mineral salts are filtered off and the solution is concentrated to dryness by evaporation. The remaining residue is dissolved in methylene chloride, filtered once again and the filtrate is in turn concentrated to dryness by evaporation. 200 ml acetone are added to the residue, whereby 17.5 g yellow 2-methyl-1-(4-nitrophenyl)-6,7-dihydro-1H,5H-pyrazolo(5,1-b)-1,3) oxazin-8-ium-chloride are separated out. The acetone solution is concentrated by evaporation, and the residue is boiled in methanol for 2 days, whereby a further 4 g of the same immonium salt are obtained. Total yield 21.5 g; melting point: 218°–220° C.

(B) A suspension of 6 g of the immonium salt described under A), 5 ml triethylamine and 3.9 g 1-(4-methyl-pyrid-2-yl)-piperazine in 100 ml toluene is heated with stirring for 10 hours under reflux. For working up, after cooling, the triethylamine hydrochloride is removed by filtration and the toluene solution is extracted with 100 ml 10% hydrochloric acid solution. The acidic aqueous solution is made alkaline by the addition of 30% sodium hydroxide solution, whereby, an oil is separated out, which through the addition of ethanol is brought to crystallization. 7 g of crude produce are obtained, which after recrystallization from benzene produce 5.7 g pure 5-methyl-1-(4-nitrophenyl)-2- {3-[4-(4-methyl-pyrid-2-yl)-piperazin-1-yl]-propyl}-pyrazolin-3-one; melting point: 160° C.

EXAMPLE 3

5-methyl-1-phenyl-2-{2-[4-(3,4-dimethoxyphenyl)-piperazin-1-yl]-ethyl}-pyrazolin-3-one (A) A sodium methylate solution, obtained from 3.9 g sodium and 80 ml methanol is added to a suspension of 26.1 g 5-methyl-1-phenylpyrazolin-3-one in 200 ml methanol. After stirring for 30 minutes, 43.02 g 1-bromo-2-chloroethane are added to the clear solution at ambient temperature. The reaction mixture is heated for 15 hours under reflux. Then the solvent is drawn off under reduced pressure. The residue which remains is dissolved in 250 ml methylene chloride and 100 ml water. The organic phase is separated off, dried over sodium sulphate, filtered, and the solvent is evaporated off under reduced pressure. The residue is dissolved in ethyl ether, and the solution is filtered to remove the remaining initial material. Then the solvent is evaporated and the residue (27 g) is boiled in 100 ml butanol or 8 hours under reflux. Finally, the solvent is evaporated in a vacuum and the residue is purified by column chromatography over silica gel. 20 g 2-(2-chloroethyl)-5-methyl-1-phenylpyrazolin-3-one are obtained as an oil.

(B) 3.71 g 2-(2-chloroethyl)-5-methyl-1-phenyl-pyrazolin-3-one are heated in 120 ml toluene with 3.5 g 1-(3,4-dimethoxyphenyl)piperazine, 2.65 g potassium carbonate and 0.5 g potassium iodide with stirring for 24 hours under reflux. After cooling, the toluene phase is extracted with 25% aqueous hydrochloric acid solution. The aqueous solution is made alkaline by the addition of 30% sodium hydroxide solution and is then extracted with 100 ml methylene chloride. The methylene chloride phase is dried over sodium sulphate, filtered, and the solvent removed under reduced pressure. The remaining residue is purified over a silica gel column and 2.5 g of the pure title compound are obtained as an oil. For conversion into its salt, the base is dissolved in a little isopropanol and the solution is mixed with a quantity of a 2.15 N solution of HCl in isopropanol, corresponding to a 10% excess of HCl, with cooling. The trihydrochloride which is formed is drawn off and crystallized from isopropanol. 2.3 g 5-methyl-1-phenyl-2-{2-[4-(3,4-dimethoxyphenyl)-piperazin-1-yl]-ethyl}-pyrazolin-3-one trihydrochloride are obtained, melting point: 140°–150° C.

EXAMPLE 4

5-methyl-1-phenyl-2-{4-[4-(4-methyl-pyrid-2-yl)-piperazin-1-yl]-butyl}-pyrazolin-3-one (A) 87 g 5-methyl-1-phenylpyrazolin-3-one are suspended in 300 ml methanol. A sodium methylate solution obtained from 13 g sodium in 300 ml methanol is added to the suspension with stirring. After 15 minutes, 87 g 1-bromo-3-chloropropane are added dropwise to the resulting clear solution. The solution is heated for 24 hours under reflux. After cooling, the mineral salts are filtered off, the solvent is then distilled off in vacuum, and the residue which remains is dissolved in 500 ml methylene chloride. The organic solution is washed with 100 ml water. The washing water is again extracted three times with 100 ml methylene chloride in each case, and the combined methylene chloride phases are dried over sodium sulphate and filtered. After the solvent is evaporated off in vacuum, 98 g residue are obtained. This residue is suspended in 200 ml acetone, and the suspension is heated for 5 minutes under reflux and is then cooled with stirring. The 2-methyl-1-phenyl-6,7-dihydro-1H, 5H-pyrazolo(5,1-b)(1,3)oxazin-8-ium chloride which results in crystalline form is filtered off. In addition, the washing waters are concentrated to dryness by evaporation, and the resulting residue is extracted with 400 ml methylene chloride. The methylene chloride solution is filtered off from the mineral salts, the solvent is distilled off under reduced pressure, and the remaining residue is treated with boiling acetone. A further quantity of the same immonium salt is obtained. Total yield 78 g; melting point: 222° C.

(B) 25.07 g of the immonium salt described under (A) are heated with 5 g sodium cyanide in 500 ml dimethyl formamide for 6 hours with stirring under reflux. Then the solvent is removed under reduced pressure, the residue is dissolved in 200 ml methylene chloride and 100 ml water, and the organic phase is separated off and dried over sodium sulphate. After concentrating the solvent by evaporation, 19 g crude 2-(3-cyanopropyl)-5-methyl-1-phenylpyrazolin-3-one remain as oily residue. The latter is used without further purification in the following reaction.

(C) 19 g of the crude nitrile obtained above are heated in 234 ml 33% aqueous hydrochloric acid for 6 hours under reflux. After cooling, sodium carbonate is added to the aqueous phase until the mixture reacts in an alkaline manner, and then the mixture is extracted with methylene chloride. The aqueous phase is separated off, acidified with concentrated hydrochloride acid to a pH of 2, and the crude carboxylic acid which precipitates out is filtered off under suction and washed with water. After recrystallization from water, 13.5 g of pure 4-[5-methyl-1-phenyl-3-oxo)pyrazolin-2-yl]-butyric acid are obtained, melting point: 145° C.

(D) A solution of 8.2 g chloroformic acid ethyl ester in 42 ml chloroform is added dropwise within 30 minutes at 0° C to a mixture of 13 g of the carboxylic acid obtained above and 11.67 ml triethylamine in 242 ml chloroform. At the same temperature, a solution of 9.4 g 1-(4-methyl-pyrid-2-yl)-piperazine and 11.67 ml triethylamine in 42 ml chloroform is then added dropwise within 30 minutes. The solution is left to heat up to ambient temperature and is stirred for 2 hours at ambient temperature. For working up, 250 ml water are added, the organic phase is separated off, dried over sodium sulphate, and the solvent is distilled off. 30 g oily raw product are obtained as residue. After washing the raw product with diethylether, ether, 24 g oily 5-methyl-1-phenyl-2-{3-[4(4-methylpyrid-2-yl)-piperazin-1-yl-carbonyl]-propyl}-pyrazoline-3-one are obtained.

(E) 16 g of the amide obtained above are added to 370 ml diethylene glycol-dimethylether, and 14.5 g sodium borohydride are added to this mixture with stirring at a temperature of under 10° C. within 30 minutes. At the same temperature, within a further 30 minutes, 22 ml acetic acid are added dropwise. The solution is then heated for 6 hours under reflux. After cooling to ambient temperature, the mixture is hydrolyzed with water. 150 ml 50% hydrochloric acid solution are added to the obtained suspension with stirring. The solution is stirred for 4 hours at ambient temperature. Then the water is evaporated off and the residue is extracted with a water/toluene mixture. The aqueous phase is separated off, made alkaline through the addition of sodium carbonate, and the formed title base is extracted with methylene chloride. The residue remaining after the solvent is evaporated off is purified chromotographically over silica gel, and 4.8 g 5-methyl-1-phenyl-2-{4-[4-(4-methyl-pyrid-2-yl)piperazin-1-yl]-butyl}-pyrazolin-3-one are obtained. The base is converted into its trihydrochloride, and this is crystallized from isopropanol. Melting point: 220° C.; yield 4.0 g.

EXAMPLE 5

5-methyl-1-phenyl-2-{3-[4-(4-methyl-pyrid-yl)-piperazin-1-yl]-propyl}-pyrazolin-3-one (A) 25 g 2-methyl-1-phenyl-6,7-dihydro-1H,5H-pyrazolo-(5,1-b)(1,3)-oxazin-8-ium chloride (produced in a manner analogous to Example 4A), 12 g N-formyl-piperazine and 33.2 g potassium carbonate are heated in 300 ml toluene for 16 hours with stirring under reflux. After cooling, the mineral salts are filtered off, and the toluene solution is concentrated to dryness by evaporation. 30 g 5-methyl-1-phenyl-2-[3-(4-formylpiperazin-1-yl)-propyl]-pyrazolin-3-one are obtained as an oily residue.

(B) The formyl compound obtained above is heated in 600 ml 10% aqueous hydrochloric acid for 9 hours under reflux. Then the reaction solution is neutralized by the addition of ammonium hydroxide, is concentrated by evaporation and extracted with 200 ml absolute ethanol. The solvent is distilled off under reduced pressure, and 18 g 5-methyl-1-phenyl-2-[3-(piperazin-1-yl)-propyl]-pyrazolin-3-one hydrochloride are obtained.

(C) 3.4 g of the hydrochloride obtained above are heated with 1.7 g 2-bromo-4-methylpyridine and 3 g triethylamine in 80 ml toluene for 24 hours under reflux. After cooling, the salts which are formed are filtered off, and the toluene phase is extracted with 50 ml 25% aqueous hydrochloric acid. The aqueous phase is made alkaline by the addition of 30% sodium hydroxide solution and extracted with methylene chloride. The methylene chloride phase is dried and concentrated to dryness by evaporation. The title base remaining as residue is recrystallized from diethylether. 2.5 g 5-methyl-1-phenyl-2-{3-[4-(4-methylpyrid-2-yl)-piperazin-1-yl]-propyl}-pyrazolin-3-one are obtained, melting point: 107°–108° C.

EXAMPLE 6

5-methyl-1-(4-carboxyphenyl)-2-{3-[4-(4-methyl-pyrid-2-yl)-piperazin-1-yl]-propyl}-pyrazolin-3-one 11 g 5-methyl-1-(4-methoxycarbonylphenyl)-2-{3-[4-(4-methyl-pyrid-2-yl)-piperazin-1-yl]-propyl}-pyrazolin-3-one hydrochloride (see Example No. 48 infra, produced in an analogous manner to Example 2A and B starting from 5-methyl-1-(4-methoxycarbonylphenyl) pyrazolin-3-one) are dissolved in 100 ml 85% ethanol, and the solution is mixed with 5 g potassium hydroxide with stirring at ambient temperature. After completion of the reaction, the reaction mixture is neutralized by the addition of pure hydrochloric acid, and the ethanol is distilled off. The remaining aqueous solution is acidified to a pH of 2 with hydrogen chloride, then the water is distilled off and the residue is dissolved in ethanol. The precipitated mineral salts are removed by suction filtration, and the filtrate is cooled, whereupon the dihydrochloride of the title compound crystallizes out. 6.3 g 5-methyl-1-(4-carboxyphenyl)-2-{3-[4-(4-methyl-pyrid-2-yl)-piperazin-1-yl]-propyl}-pyrazolin-3-one dihydrochloride are obtained, melting point: 205°–225° C.

EXAMPLE 7

5-methyl-1-(4-hydroxyphenyl)-2-{3-[4-(4-methyl-pyrid-2-yl)-piperazin-1-yl]-propyl}-pyrazolin-3-one 2 g 5-methyl-(4-methoxyphenyl)-2-{3-[4-(4-methyl-pyrid-2yl)-piperazin-1-yl]-propyl}-pyrazolin-3-one (see Example No. 47 infra, produced in an analogous manner to Example 2A and B starting from 5-methyl-1-(4-methoxy-phenyl)-pyrazolin-3-one) are added at a temperature of 120¼C. to pyridinium chloride obtained by mixing 9.1 ml pyridine with 10 ml concentrated hydrochloric acid and subsequent evaporation of water. The mixture is heated to a temperature of 210° C for 30 minutes and then cooled to ambient temperature. 20 ml water are added to the reaction mixture which is neutralized with a sodium hydroxide solution, and the oil which is formed is extracted with chloroform. The chloroform extract is dried over sodium sulphate, and the solvent is distilled off. After the addition of diethylether to the residue, the title base crystallized out. 0.7 g 5-methyl-1-(4hydroxy-phenyl-2-{3-[4-(4-methyl-pyrid-2-yl)piperazin-1-yl]-propyl}-pyrazolin-3-one are obtained, melting point: 170° C.

According to the methods described in the method examples, the 5-alkyl-1-phenyl-2-piperazinoalkyl-pyrazolin-3-one compounds of Formula I listed in the following Table 1 may also be prepared from corresponding compounds of Formulae II, III, V or VII.

According to the methods described in Examples 1A, 2A and 4A, the immonium salts of Formula III listed in the following Table 2 may be prepared from the corresponding 5-alkyl-1-phenylpyrazolin-3-ones of Formula VIII.

TABLE 1

| Example No. | $R_1$ | $R_2$ | $R_3$ | Z | $R_4$ | Salt | M.P. °C. |
|---|---|---|---|---|---|---|---|
| 8 | $CH_3$ | H | H | $n-C_3H_6$ | 4-F—phen | 2,7HCl | 142 |
| 9 | $CH_3$ | H | H | $n-C_3H_6$ | 3-$CH_3$OCO—2-pyr | 2,8HCl | 162 |
| 10 | $CH_3$ | H | H | $n-C_3H_6$ | 2-$CH_3$O—phen | 3HCl | 151 |
| 11 | $CH_3$ | H | H | $n-C_3H_6$ | phen | 2HCl | 138–144 |
| 12 | $n-C_3H_7$ | H | H | $n-C_3H_6$ | 4-F—phen | 2,9HCl | 140–142 |
| 13 | $n-C_3H_7$ | H | H | $n-C_3H_6$ | 4-$CH_3$—2-pyr | 3,8HCl | 164 |
| 14 | $C_2H_5$ | H | H | $n-C_3H_6$ | 3-$CF_3$—phen | 3,3HCl | 150 |
| 15 | Cyclohex | H | H | $n-C_3H_6$ | 4-$CH_3$—2-pyr | 4HCl | 150 |
| 16 | $CH_3$ | 3-$CF_3$ | H | $n-C_3H_6$ | 4-F—phen | 2,9HCl | 140 |
| 17 | $CH_3$ | 2-$CH_3$OCO | H | $n-C_3H_6$ | 4-$CH_3$—2-pyr | 3HCl | 160 |
| 18 | $CH_3$ | 4-Cl | H | $n-C_3H_6$ | 4-$CH_3$—2-pyr | 3HCl | 168–172 |
| 19 | $CH_3$ | 2,5-di-Cl | H | $n-C_3H_6$ | 4-$CH_3$—2-pyr | 2,5HCl | 130 |
| 20 | $CH_3$ | 4-$CH_3$ | 2-Cl | $n-C_3H_6$ | 4-$CH_3$O—phen | Ba | 110–112 |
| 21 | $CH_3$ | 2-$CH_3$O | H | $n-C_3H_6$ | 4-$CH_3$—2-pyr | 3HCl | 165–170 |
| 22 | $n-C_3H_7$ | 3,4-di-Cl | | $n-C_3H_6$ | 4-F—phen | HCl | 172–180 |
| 23 | $C_2H_5$ | 4-Cl | H | $n-C_3H_6$ | 4-$CH_3$—2-pyr | 3HCl | 200–205 |
| 24 | $CH_3$ | H | H | $n-C_3H_6$ | 6-$CH_3$O—2-pyr | 2HCl | 162 |
| 25 | $CH_3$ | H | H | $n-C_3H_6$ | 5-$NO_2$—2-pyr | Ba | 140 |
| 26 | $n-C_6H_{13}$ | H | H | $n-C_3H_6$ | 4-$CH_3$—2-pyr | 3HCl | 176 |
| 27 | Cyclohex | H | H | $n-C_3H_6$ | 4-Cl—phen | 2HCl | 150 |
| 28 | $CH_3$ | H | H | $n-C_3H_6$ | 4-$CH_3$CO—phen | Fu | 136 |
| 29 | $CH_3$ | 4-$NO_2$ | H | $n-C_3H_6$ | 2-pyr | 3HCl | 135–145 |
| 30 | $CH_3$ | 4-$C_2H_5$O | H | $n-C_3H_6$ | 3-Cl—6-$CH_3$—phen | Ba | 119 |
| 31 | $(CH_3)_2$—CH—$CH_2$ | H | H | $n-C_3H_6$ | 2-F—phen | 2HCl | 130–135 |
| 32 | $CH_3$ | H | H | $n-C_3H_6$ | 5-$CH_3$—2-pyr | Ba | 115 |
| 33 | $CH_3$ | H | H | $CH_2$—CH—$CH_2$<br>        |<br>        $CH_3$ | 4-$CH_3$—2-pyr | 3HCl | 164–168 |
| 34 | $CH_3$ | 3-Br | H | $n-C_3H_6$ | 4-$CH_3$—2-pyr | 3,6HCl | 168 |
| 35 | $CH_3$ | 4-$CH_3$OCO | H | $n-C_3H_6$ | 4-F—phen | HCl | 157–163 |
| 36 | $CH_3$—$CH_2$—CH<br>        |<br>        $CH_3$ | H | H | $n-C_3H_6$ | 5-Cl—2-pyr | 2,7HCl | 160 |
| 37 | $C_2H_5$ | H | H | $n-C_3H_6$ | 4-$CH_3$—2-pyr | 3HCl | 184 |
| 38 | $C_2H_5$ | 4-$NO_2$ | H | $n-C_3H_6$ | 4-$CH_3$—2-pyr | Ba | 113 |
| 39 | $CH_3$ | 4-$NO_2$ | H | $n-C_3H_6$ | 4-F—phen | 2HCl | 170–180 |
| 40 | $CH_3$ | 2-F | H | $CH_2$—$CH_2$—CH<br>              |<br>              $CH_3$ | 3-Cl—phen | Ba | oil |
| 41 | $C_2H_5$ | 3-$CF_3$ | H | $CH_2$—CH—$CH_2$<br>        |<br>        $CH_3$ | 4-$CH_3$—2-pyr | Ba | oil |
| 42 | $CH_3$ | 2-F | H | CH—$CH_2$—$CH_2$<br>|<br>$CH_3$ | 3-Cl—phen | Ba | oil |
| 43 | Cycloprop | H | H | $n-C_3H_6$ | 4-F—phen | Ba | 127–128 |
| 44 | $CH_3$ | 4-$CH_3$CO | H | $n-C_3H_6$ | 4-$CH_3$—2-pyr | 3HCl | 210 |
| 45 | $CH_3$ | H | H | $n-C_3H_6$ | 2-pyr | 3HCl.1$H_2$O | 130 |
| 46 | $CH_3$ | 4-CN | H | $n-C_3H_6$ | 4-$CH_3$—2-pyr | 2,4HCl | 200–210 |
| 47 | $CH_3$ | 4-$CH_3$O | H | $n-C_3H_6$ | 4-$CH_3$—2-pyr | 2,6HCl | 200–205 |
| 48 | $CH_3$ | 4-$CH_3$OCO | H | $n-C_3H_6$ | 4-$CH_3$—2-pyr | HCl.0,5$H_2$O | 115–125 |
| 49 | Cyclohex | H | H | $n-C_3H_6$ | 4-F—phen | 2,4HCl | 160–170 |
| 50 | $C_2H_5$ | H | H | $CH_2$—CH—$CH_2$<br>        |<br>        $CH_3$ | 4-F—phen | Ba | 129–130 |
| 51 | Cyclohex | H | H | $CH_2$—CH—$CH_2$<br>        |<br>        $CH_3$ | 4-$CH_3$—2-pyr | Ba | 80–90 |
| 52 | $CH_3$ | H | H | $n-C_4H_8$ | 2,6-di-$CH_3$—phen | 2HCl | 182 |
| 53 | $CH_3$ | 4-COO$C_2H_5$ | H | $n-C_3H_6$ | 4-$CH_3$—2-pyr | HCl.0,5$H_2$O | 169–170 |
| 54 | $C_2H_5$ | 4-$NO_2$ | H | $n-C_3H_6$ | 4-F—phen | 1,2HCl | 185–190 |
| 55 | $CH_3$ | 4-$CH_3$ | H | $n-C_3H_6$ | 4-$CH_3$—2-pyr | 1,1HCl | 190–195 |
| 56 | $CH_3$ | 3,4-di-OCH_3 | | $n-C_3H_6$ | 4-$CH_3$—2-pyr | 2,6HCl.0,3$H_2$O | 205–210 |
| 57 | $CH_3$ | 3,4-O—$CH_2$—$CH_2$—O | | $n-C_3H_6$ | 4-$CH_3$—2-pyr | 1,6HCl.0,3$H_2$O | 200–205 |
| 58 | Cyclopent | H | H | $n-C_3H_6$ | 4-$CH_3$—2-pyr | 2,7HCl | 162–164 |
| 59 | $CH_3$ | 4-$COCH_3$ | | $n-C_3H_6$ | 4-F—phen | Ba | 107–110 |
| 60 | $CH_3$ | 4-CN | | $n-C_3H_6$ | 4-F—phen | Ba | 116–117 |
| 61 | $CH_3$ | 4-$OCH_3$ | | $n-C_3H_6$ | 4-F—phen | Ba | 132–133 |
| 62 | $CH_3$ | 4-Cl | | $n-C_3H_6$ | 4-F—phen | Ba | 84–86 |

TABLE 1-continued

| Example No. | $R_1$ | $R_2$ | $R_3$ | Z | $R_4$ | Salt | M.P. °C. |
|---|---|---|---|---|---|---|---|
| 63 | Cyclopent | H | H | $nC_3H_6$ | 4-F—phen | 1,8HCl | 140-150 | pyr = Pyridyl, phen = Phenyl, Cyclohex = Cyclohexyl, Cycloprop = Cyclopropyl, Cyclopent = Cyclopentyl, HCl = Hydrochlorid, Ba = Base, Fu = mono-fumarate

TABLE 2

| Example No. | $R_1$ | $R_2$ | $R_3$ | Z | Y | M.P. °C. |
|---|---|---|---|---|---|---|
| 12A | $n-C_3H_7$ | H | H | $n-C_3H_6$ | Cl | 175-176 |
| 15A | Cyclohex | H | H | $n-C_3H_6$ | Cl | 246 |
| 16A | $CH_3$ | 3-$CF_3$ | H | $n-C_3H_6$ | Cl | 228 |
| 17A | $CH_3$ | 2-$CH_3OCO$ | H | $n-C_3H_6$ | Cl | 218-220 |
| 18A | $CH_3$ | 4-Cl | H | $n-C_3H_6$ | Cl | 188 |
| 18A' | $CH_3$ | 4-Cl | H | $n-C_3H_6$ | Br | 198-200 |
| 19A | $CH_3$ | 2,5-di-Cl | | $n-C_3H_6$ | Cl | 232 |
| 20A | $CH_3$ | 2-Cl—4-$CH_3$ | | $n-C_3H_6$ | Cl | 212-213 |
| 21A | $CH_3$ | 2-$CH_3O$ | H | $n-C_3H_6$ | Cl | 205-206 |
| 22A | $n-C_3H_7$ | 3,4-di-Cl | | $n-C_3H_6$ | Cl | 248-250 |
| 23A | $C_2H_5$ | 4-Cl | H | $n-C_3H_6$ | Cl | 168 |
| 26A | $n-C_6H_{13}$ | H | H | $n-C_3H_6$ | Cl | 118 |
| 30A | $CH_3$ | 4-$C_2H_5O$ | H | $n-C_3H_6$ | Cl | 144 |
| 31A | $(CH_3)_2$—CH—$CH_2$ | H | H | $n-C_3H_6$ | Cl | 192 |
| 33A | $CH_3$ | H | H | $CH_2$—CH—$CH_2$<br>\|<br>$CH_3$ | Cl | 176 |
| 34A | $CH_3$ | 3-Br | H | $n-C_3H_6$ | Cl | 200 |
| 35A | $CH_3$ | 4-$CH_3OCO$ | H | $n-C_3H_6$ | Cl | 184-186 |
| 36A | $CH_3$—$CH_2$—CH<br>\|<br>$CH_3$ | H | H | $n-C_3H_6$ | Cl | 214-215 |
| 38A | $C_2H_5$ | 4-$NO_2$ | H | $n-C_3H_6$ | Cl | 205-210 |
| 41A | $C_2H_5$ | 3-$CF_3$ | H | $CH_2$—CH—$CH_2$<br>\|<br>$CH_3$ | Cl | 176 |
| 43A | Cycloprop | H | H | $n-C_3H_6$ | Cl | 148-150 |
| 44A | $CH_3$ | 4-$CH_3CO$ | H | $n-C_3H_6$ | Cl | 177-180 |
| 46A | $CH_3$ | 4-CN | H | $n-C_3H_6$ | Cl | 120-130 |
| 47A | $CH_3$ | 4-$CH_3O$ | H | $n-C_3H_6$ | Cl | 203 |
| 50A | $C_2H_5$ | H | H | $CH_2$—CH—$CH_2$<br>\|<br>$CH_3$ | Cl | 144-145 |
| 51A | Cyclohex | H | H | $CH_2$—CH—$CH_2$<br>\|<br>$CH_3$ | Cl | 220-222 |
| 55A | $CH_3$ | 4-$CH_3$ | H | $n-C_3H_6$ | Cl | 207-208 |
| 56A | $CH_3$ | 3,4-di-$OCH_3$ | | $n-C_3H_6$ | Cl | ha,—140 |
| 57A | $CH_3$ | 3,4-O—$CH_2$—$CH_2$—O | | $n-C_3H_6$ | Cl | 215-220 |
| 58A | Cyclopent | H | H | $n-C_3H_6$ | Cl | 214-215 |

Cyclohex = Cyclohexyl, Cycloprop = Cyclopropyl, Cyclopent = Cyclopentyl, se = semi-solid The following Table 3 lists as starting materials for synthesis of the componds of Formula III, examples of new 5-alkyl-1-phenyl-pyrazolin-3-ones of Formula VIII which can bed produced according to methods known from the literature.

TABLE 3

| Substance No. | $R_1$ | $R_2$ | $R_3$ | M.P. °C. |
|---|---|---|---|---|
| 101 | $C_2H_5$ | H | H | 143-144 |
| 102 | $n-C_3H_7$ | H | H | 136-138 |
| 103 | $(CH_3)_2$—CH—$CH_2$ | H | H | 180 |
| 104 | $CH_3$—$CH_2$—CH<br>\|<br>$CH_3$ | H | H | 166-167 |
| 105 | $(CH_3)_3C$ | H | H | 144 |
| 106 | $n-C_6H_{13}$ | H | H | 130 |
| 107 | Cycloprop | H | H | 148 |
| 108 | Cyclohex | H | H | 243 |
| 109 | $CH_3$ | 4-$CH_3CO$ | H | 216 |
| 110 | $CH_3$ | 4-$C_2H_5O$ | H | 170-171 |
| 111 | $CH_3$ | 4-$C_2H_5OCO$ | H | 211 |
| 112 | $CH_3$ | 3-Br | H | 205 |

TABLE 3-continued

| Substance No. | $R_1$ | $R_2$ | $R_3$ | M.P. °C. |
|---|---|---|---|---|
| 113 | $CH_3$ | 3-$CF_3$ | H | 165 |
| 114 | $CH_3$ | 2-F | H | 201 |
| 115 | $CH_3$ | 2-Cl—4-$CH_3$ |  | 209–210 |
| 116 | $C_2H_5$ | 4-Cl | H | 198 |
| 117 | $C_2H_5$ | 4-$NO_2$ | H | 264 |
| 118 | $C_2H_5$ | 3-$CF_3$ | H | 160 |
| 119 | n-$C_3H_7$ | 3,4-di-Cl |  | 183–184 |
| 120 | $CH_3$ | 4-CN | H | 255 |
| 121 | $CH_3$ | 4-$CH_3O$ | H | 195–200 |
| 122 | Cyclopent | H | H | 212–213 |
| 123 | $CH_3$ | 3,4-di-$OCH_3$ |  | 160–162 |
| 124 | $CH_3$ | 3,4-O—$CH_2$—$CH_2$—O |  | 242–245 |

Cyclohex = Cyclohexyl, Cyclopent = Cyclopentyl, Cycloprop = Cyclopropyl

The invention will now be further illustrated by the following Example of a pharmaceutical preparation.

EXAMPLE I—TABLETS

Tables are produced with the following composition per tablet:

| | |
|---|---|
| 5-ethyl-1-phenyl-2-{3-[4-(-fluorophenyl)-piperazin-1-yl]-propyl}-pyrazolin-3-one | 15 mg |
| Maize starch | 60 mg |
| Lactose | 140 mg |
| Gelatine (as 10% solution) | 6 mg |

The active substance, the maize starch and the lactose are thickened with the 10% gelatine solution, the paste is comminuted, and the resulting granulate is placed onto a suitable sheet and dried at 45° C. The dried granulate is passed through a crushing machine and mixed in a mixer with the following further adjuvant substances:

| | |
|---|---|
| Talcum | 5 mg |
| Magnesium stearate | 5 mg |
| Maize starch | 9 mg | and is then compressed to tablets each of 240 mg.

What is claimed is:

1. A 5-alkyl-1-phenyl-2-piperazinoalkyl -pyrazolin-3-one compound of the Formula I

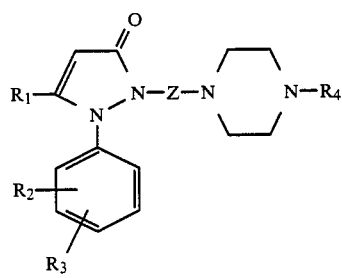

in which
$R_1$ is a straight-chain, branched or cyclic alkyl group with up to 6 carbon atoms,
$R_2$ is hydrogen, halogen, trifluoromethyl, nitro, cyano, hydroxy, primary or secondary lower alkyl, lower alkoxy, or an $R_5$—CO— group, in which $R_5$ is lower alkoxy, lower alkyl or hydroxy, and
$R_3$ is hydrogen, halogen, primary or secondary lower alkyl or lower alkoxy, or
$R_2$ and $R_3$ are linked to adjacent carbon atoms and together form an alkylene-dioxy group with 1 or 2 carbon atoms,
Z is an alkylene chain with 2 to 4 carbon atoms,
$R_4$ is a phenyl group of Formula a or a pyridyl group of Formula b,

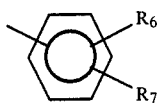 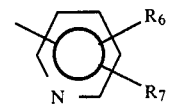

(a)        (b)

in which
$R_6$ is hydrogen, halogen, trifluoromethy, nitro, cyano, hydroxy, primary or secondary lower alkyl, lower alkoxy or an $R_5$—CO— group in which $R_5$ has the above meaning, and
$R_7$ is hydrogen, halogen, primary or secondary lower alkyl or lower alkoxy;
and its pharmacologically acceptable acid addition salts.

2. A 5-alkyl-1-phenyl-2-piperazinoalkylpyrazolin-3-one compound according to claim 1, in which
$R_2$ is hydrogen, halogen, cyano, nitro, hydroxy, lower alkyl, lower alkoxy, lower alkylcarbonyl or lower alkoxycarbonyl and
$R_3$ is hydrogen, halogen or lower alkoxy, or
$R_2$ and $R_3$ are linked to adjacent carbon atoms and together form an alkylene dioxy group with 1 or 2 carbon atoms,
$R_4$ is a phenyl group of Formula a, in which
$R_6$ is hydrogen, halogen, lower alkoxy, primary or secondary lower alkyl or trifluoromethyl and
$R_7$ is hydrogen, halogen, primary or secondary lower alkyl or lower alkoxy or
$R_4$ is a pyridyl group of Formula b, in which
$R_6$ is hydrogen, lower alkyl or halogen and
$R_7$ is hydrogen.

3. A 5-alkyl-1-phenyl-2-piperazinoalkylpyrazolin-3-one compound according to claim 2, in which
Z is an alkylene chain with 3 or 4 carbon atoms,
$R_2$ is hydrogen, halogen, cyano, nitro, lower alkoxy or lower alkylcarbonyl,
$R_3$ is hydrogen, and
$R_4$ is a phenyl group, which is unsubstituted or is substituted by halogen, or
$R_4$ is a 2-pyridyl group which is unsubstituted or is substituted by lower alkyl.

4. A 5-alkyl-1-phenyl-2-piperazinoalkylpyrazolin-3-one compound according to claim 3, in which $R_2$ is hydrogen, nitro, chlorine, cyano, methoxy or acetyl and $R_3$ is hydrogen, Z is a propylene chain, and $R_4$ is the 4-methyl-2-pyridyl group or the 4-fluorophenyl group.

5. A 5-alkyl-1-phenyl-2-piperazinoalkylpyrazolin-3-one compound according to claim 4, in which $R_1$ is a straight-chain or branched alkyl group with 1 to 4 carbon atoms or a cyclic alkyl group with 5 or 6 carbon atoms.

6. A 5-alkyl-phenyl-1- {3-[4-(4-methylpyrid-2-yl)-piperazin-1-yl]-propyl}-pyrazolin-3-one compound according to claim 5, the 1-phenyl ring of which is unsubstituted or is substituted in position 4 by chlorine, nitro or methoxy, and the 5-alkyl group of which is methyl, ethyl, n-propyl, cyclopentyl or cyclohexyl.

7. A 5-alkyl -1-phenyl-2-{3-[4-(4-fluorophenyl)-piperazin-1-yl]-propyl}-pyrazolin-3-one compound according to claim 5, the 1-phenyl ring of which is unsubstituted or is substituted in position 4 by nitro and the 5-alkyl group of which is methyl, ethyl, n-propyl, cyclopropyl, cyclopentyl or cyclohexyl.

8. A pharmaceutical preparation containing an antiallergically effective amount of a 5-alkyl-1-phenyl-2-piperazinoalkylpyrazolin-3-one compound according to claim 1 and at least one conventional pharmaceutical solid or liquid carrier or diluent.

9. 5-ethyl-1-phenyl-2{-3-[4-(4-fluorophenyl)-piperazin-1-yl]-propyl}-pyrazolin-3-one according to claim 1 and its pharmacologically acceptable acid addition salts.

10. 5-methyl-1-(4-nitrophenyl)-2-{3-[4-(4-methyl- pyrid-2-yl)-piperazin-1-yl]-propyl}-pyrazolin-3-one according to claim 1 and its pharmacologically acceptable acid addition salts.

11. 5-methyl-1-phenyl-2-{3-[4-(4-methyl-pyrid-2-yl)-piperazin-1-yl]-propyl}-pyrazolin-3-one according to claim 1 and its pharmacologically acceptable acid addition salts.

12. 5-(n-propyl)-1-phenyl-2-{3-[4-(4-methyl-pyrid-2-yl)-piperazin-1-yl]-propyl}-pyrazolin-3-one according to claim 1 and its pharmacologically acceptable acid addition salts.

13. 5-cyclohexyl-1-phenyl-2-{3-[4-(4-methyl-pyrid-2-yl)-piperazin-1-yl]-propyl}-pyrazolin-3-one according to claim 1 and its pharmacologically acceptable acid addition salts.

14. 5-methyl-1-(4-chlorophenyl)-2-{3-[4-(4-methyl-pyrid-2-yl)-piperazin-1-yl]-propyl}-pyrazolin-3-one according to claim 1 and its pharmacologically acceptable acid addition salts.

15. 5-ethyl-1-(4-nitrophenyl)-2-{3-[4-(4-methyl-pyrid-2-yl)-piperazine-1-yl]-propyl}-pyrazolin-3-one according to claim 1 and its pharmacologically acceptable acid addition salts.

16. 5-methyl-1-(4-nitrophenyl)-2-{3-[4-(4-fluorophenyl)-piperazin-1-yl]-propyl}-pyrazolin-3-one according to claim 1 and its pharmacologically acceptable acid addition salts.

17. 5-cyclohexyl-1-phenyl-2-{3-[4-(4-fluorophenyl)-piperazin-1-yl]-propyl}-pyrazolin-3-one according to claim 1 and its pharmacologically accetpable acid addition salts.

18. 5-methyl-1-(4-cyanophenyl)-2-{3-[4-(4-fluorophenyl)-piperazin-1-yl]-propyl}-pyrazolin-3-one according to claim 1 and its pharmacologically acceptable acid addition salts.

19. 5-methyl-1-(4-chlorophenyl)-2-{3-[4-(4-fluorophenyl)-piperazin-1-yl]-propyl}-pyrazolin-3-one according to claim 1 and its pharmacologically acceptable acid addition salts.

* * * * *